US012133732B2

(12) United States Patent
Chen et al.

(10) Patent No.: US 12,133,732 B2
(45) Date of Patent: Nov. 5, 2024

(54) DISPOSABLE ECG ELECTRODE TO PREVENT SHEDDING AND TEARING

(71) Applicant: Guangren Chen, Arcadia, CA (US)

(72) Inventors: Guangren Chen, Arcadia, CA (US); Jialun Chen, Arcadia, CA (US); Rong Yang, Porter Ranch, CA (US); Jia Li Chen, Palm Harbor, FL (US)

( * ) Notice: Subject to any disclaimer, the term of this patent is extended or adjusted under 35 U.S.C. 154(b) by 0 days.

(21) Appl. No.: 17/995,900

(22) PCT Filed: Dec. 8, 2021

(86) PCT No.: PCT/US2021/062479
§ 371 (c)(1),
(2) Date: Oct. 10, 2022

(87) PCT Pub. No.: WO2022/125706
PCT Pub. Date: Jun. 16, 2022

(65) Prior Publication Data
US 2023/0293076 A1    Sep. 21, 2023

Related U.S. Application Data

(60) Provisional application No. 63/128,070, filed on Dec. 19, 2020, provisional application No. 63/123,008, filed on Dec. 9, 2020.

(51) Int. Cl.
*A61B 5/259* (2021.01)
*A61B 5/266* (2021.01)
(Continued)

(52) U.S. Cl.
CPC .............. *A61B 5/259* (2021.01); *A61B 5/266* (2021.01); *A61B 5/274* (2021.01); *A61B 5/28* (2021.01);
(Continued)

(58) Field of Classification Search
CPC ......... A61B 5/259; A61B 5/266; A61B 5/274; A61B 5/28; A61B 2560/0285; A61B 2562/125
See application file for complete search history.

(56) References Cited

U.S. PATENT DOCUMENTS

2008/0281180 A1    11/2008    Choe et al.
2013/0281814 A1    10/2013    Tilt et al.
(Continued)

FOREIGN PATENT DOCUMENTS

| WO | WO-2016010983 A1 * | 1/2016 | ........... A61B 5/6833 |
| WO | 2019/241753 A1 | 12/2019 | |
| WO | 2020/150784 A1 | 7/2020 | |

OTHER PUBLICATIONS

International Search Report and Written Opinion for PCT/US21/62479, mail Feb. 23, 2022.

*Primary Examiner* — Adam Z Minchella
(74) *Attorney, Agent, or Firm* — Kasha Law LLC; John R. Kasha; Kelly L. Kasha

(57) ABSTRACT

An ECG electrode includes a substrate and one or more holes. The substrate includes on one side an electrolyte gel for contacting a patients skin and an adhesive. The one or more holes perforate the substrate and the adhesive to increase the adhesion between the patients skin and the substrate. The one or more holes can have a circular shape, rectangular shape, crescent shape, polygonal shape, elliptical shape, diamond shape, star shape, or triangular shape. A method for manufacturing an ECG electrode includes assembling a substrate that includes on one side an electrolyte gel for contacting a patients skin and an adhesive and creating one or more holes in the substrate and the adhesive that increase the adhesion between the skin and the substrate. The one or more holes are created using a laser or a drill.

19 Claims, 25 Drawing Sheets

(51) Int. Cl.
*A61B 5/274* (2021.01)
*A61B 5/28* (2021.01)
(52) U.S. Cl.
CPC . *A61B 2560/0285* (2013.01); *A61B 2562/125* (2013.01)

(56) References Cited

U.S. PATENT DOCUMENTS

| | | | |
|---|---|---|---|
| 2013/0324828 A1* | 12/2013 | Nishiwaki | A61B 5/274 600/391 |
| 2014/0206977 A1* | 7/2014 | Bahney | A61B 5/25 600/386 |
| 2015/0359485 A1* | 12/2015 | Berg | A61B 5/24 600/388 |
| 2017/0296805 A1 | 10/2017 | Mower | |
| 2017/0333696 A1* | 11/2017 | Shibata | A61N 1/0496 |
| 2018/0020982 A1* | 1/2018 | Elsherbini | A61B 5/746 600/301 |
| 2018/0111353 A1 | 4/2018 | Huppert et al. | |
| 2018/0249767 A1* | 9/2018 | Begriche | A41F 15/002 |
| 2019/0290137 A1 | 9/2019 | Zhang et al. | |
| 2021/0259634 A1* | 8/2021 | Ginestet | A61B 5/6833 |

* cited by examiner

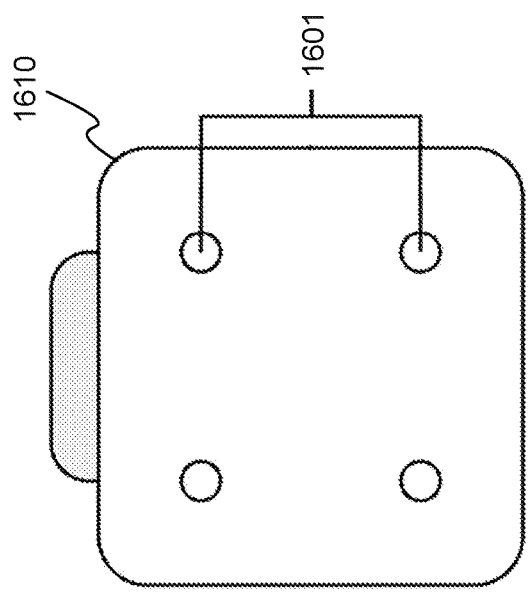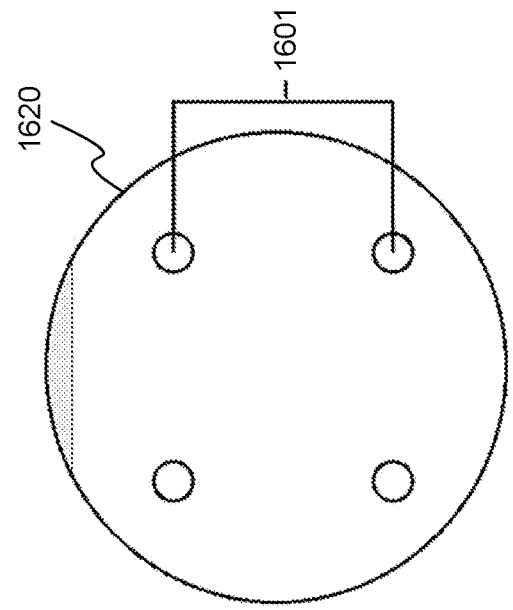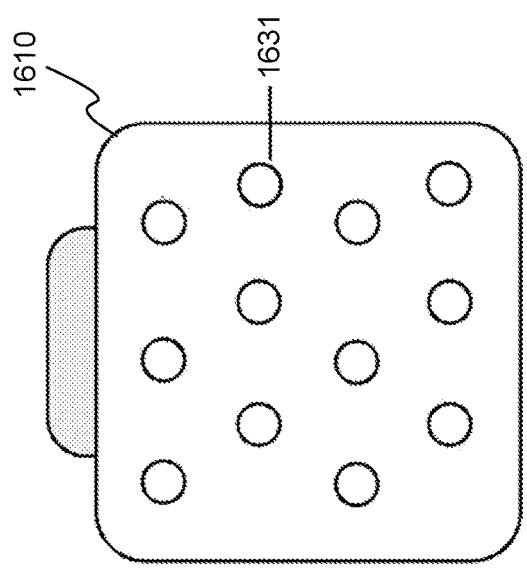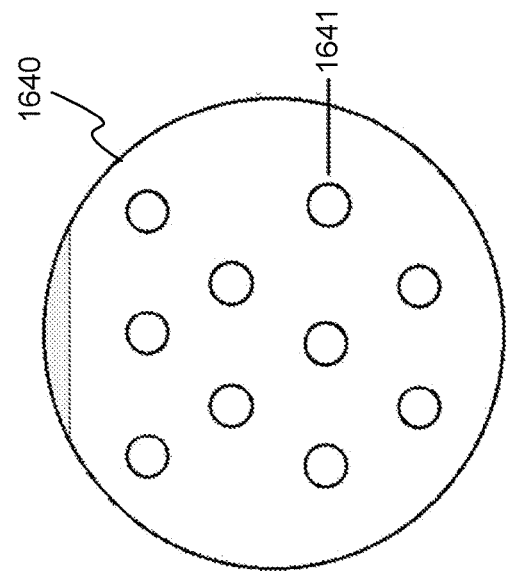
FIG. 16

2100

DISPOSABLE ECG ELECTRODE TO PREVENT SHEDDING AND TEARING

CROSS-REFERENCE TO RELATED APPLICATION

This application claims the benefit of U.S. Provisional Patent Application Ser. No. 63/123,008, filed Dec. 9, 2020 and U.S. Provisional Patent Application Ser. No. 63/128,070, filed Dec. 19, 2020, the content of all of which is incorporated by reference herein in their entireties.

INTRODUCTION

The teachings herein relate to an electrocardiography (ECG) electrode that prevents shedding or tearing away from the skin during usage and a method of manufacture for this ECG electrode. More particularly, the teachings herein relate to an ECG electrode that includes one or more holes to improve adherence of the ECG electrode to the skin and a method of manufacturing an ECG electrode to include one or more holes to improve adherence of the ECG electrode to the skin.

BACKGROUND

Types of ECG Electrodes

At present, there are two main types of disposable ECG electrodes. One is the most commonly used button, stud, or snap-type electrode. The interface of the electrode is a metal button, stud, or snap. The lead wire interface is another metal button, stud, or snap. These two snaps are connected.

FIG. 1 is a top view 100 of an exemplary snap-type ECG electrode, upon which various embodiments may be implemented. In this view, snap-type electrode 110 is shown connected to lead wire 120. Snap-type electrode 110 includes a male snap (not shown) that connects to a female snap (not shown) of lead wire 120. Snap-type electrode 110 also includes substrate 115 that is typically made of cloth or foam. Substrate 115 often includes a region 113 in which brand name advertising of the manufacturer is presented.

FIG. 2 is a bottom view 200 of an exemplary snap-type ECG electrode, upon which various embodiments may be implemented. In this view, the bottom of male snap 217 of snap-type electrode 110 is visible protruding through substrate 115. Covering the bottom of male snap 217, in this example, is a rectangular patch of electrolyte gel 219.

Typically, the male snap of a snap-type ECG electrode includes a metal electrode snap contact on the top of the electrode connected to a silver (Ag) to silver chloride (AgCl) conductor on the bottom of the electrode. The part of male snap 217 seen in FIG. 2 is, for example, the Ag to AgCl conductor.

To conduct an electrical signal from the skin, electrolyte gel 219 contacts the skin. Electrolyte gel 219 includes, for example, free chlorine (Cl$^-$) ions. In response, to an electrical signal at the surface of the skin, these free Cl$^-$ ions move towards Ag to AgCl conductor 217. In turn, Ag gives up electrons, becoming Ag$^+$ ions, and these ions move toward electrolyte gel 219 and become AgCl at the interface with electrolyte gel 219.

To obtain a correct signal from the skin, electrolyte gel 219 must make and maintain proper contact with the skin. As a result, regions outside of electrolyte gel 219 on the bottom of substrate 115 include an adhesive to secure substrate 115 to the skin.

The second type of disposable ECG electrode is the flat sheet or tab ECG electrode. The tab ECG electrode differs from the snap-type ECG electrode in that it does not include a metal button, stud, or snap. It, therefore, does not include, an Ag to AgCl conductor connected to a snap. Instead, a tab electrode includes a layer of Ag to AgCl conductor. This layer of Ag to AgCl conductor is then in contact with a layer of electrolyte gel that, in turn, contacts the skin.

Because the tab electrode does not include a metal button, stud, or snap, it is typically connected to an ECG lead wire through an alligator clip, gripper clip, or clamp. A metal portion of the alligator clip, gripper clip, or clamp makes contact with the layer of Ag to AgCl conductor at an edge of the tab electrode often formed as a distinct tab of the tab electrode.

FIG. 3 is a top view 300 of an exemplary tab-type ECG electrode, upon which various embodiments may be implemented. In this view, tab-type electrode 310 is shown connected to lead wire 320. Tab-type electrode 310 connects to lead wire 320 through clamp 330. Note that clamp 330 is often part of lead wire 320. Tab-type electrode 310 also includes substrate 115 that is typically made of cloth or foam.

Clamp 330 connects to tab-type electrode 310 by clamping tab 312 of substrate 315 of tab-type electrode 310. Substrate 315 can also include region 313 in which brand name advertising of the manufacturer is presented.

FIG. 4 is a bottom view 400 of an exemplary tab-type ECG electrode, upon which various embodiments may be implemented. In this view, the bottom of substrate 315 of tab-type electrode 310 shows a cross-hatched pattern of the layer of Ag to AgCl conductor. On top of this layer of Ag to AgCl conductor is a layer of electrolyte gel. The layer of electrolyte gel makes contact with the skin. Gaps between the cross-hatched pattern of the layer of electrolyte gel or mixed with the layer of electrolyte gel is an adhesive to secure substrate 115 to the skin.

The snap-type ECG electrode is typically used when multiple or continuous readings are required because it is easier to attach and reattach to a lead. As a result, snap-type ECG electrodes need to adhere well to the skin for longer periods of time.

The tab-type ECG electrode is typically used for single reading applications or resting tests. Consequently, tab-type ECG electrodes typically are not required to adhere to the skin for as long as snap-type ECG electrodes. However, the clips of lead wire can often exert forces on tab-type ECG electrodes causing them to tear off.

Snap-type and tab-type ECG electrodes have been used for ECG devices including, but not limited to, bedside ECGs, vital sign monitors, Holter monitors, exercise monitors, stress test monitors, special cardiac monitors, and all other non-invasive ECG monitors for the past century. Unfortunately, however, during this time, both of these types of electrodes have been plagued by adherence problems.

Adherence Problem

Adherence problems for ECG electrodes have been found in the clinic, the hospital setting, and in ECG stress testing. In the clinic, it is been found that ECG electrodes often easily fall off of the body surface. Typically this failure is not due to the interface between the lead wire and the electrode. Instead, it is due to the electrode coming loose from the surface of the skin. This loosening occurs for many different reasons including, but not limited to, light fretting, dry skin, oily skin, temperature and humidity, hair, the change of the keratin layer on the skin surface after aging, or after use for a long period of time. A primary cause of the loosening is a loss of an airtight seal between the electrode and the skin.

In the hospital setting, a primary cause of the electrode coming loose from the surface of the skin is pulling or tearing. On the operating table or in the emergency room, rescue room, ICU, CCU, SICU, NICU, or other locations in a hospital, the tubes of various other instruments on the patient's body, such as oxygen trachea, ventilator tube, infusion tube, intubation, or catheter, can collide with a lead wire, causing an electrode to fall off from the skin after pulling or tearing. This happens particularly often on the operating table and in the intensive care unit and emergency department. It can also be a cause of a medical accident.

During exercise or stress testing, a primary cause of the electrode coming loose from the surface of the skin is movement. For example, during a stress test ECG, a treadmill test, or a 24, 36, or 72 hour Holter monitoring test, exercise movement, daily movement, clothing movement, or various small movements can cause an electrode to be shed or torn off. Consequently, a great deal of testing time is lost.

As a result, there is a need for new ECG electrode products and methods of manufacture to allow ECG electrodes to more reliably adhere to the skin and provide a consistent signal to an ECG device over time.

BRIEF DESCRIPTION OF THE DRAWINGS

FIG. 16 is an exemplary diagram showing top views of four different tab-type ECG electrodes with different hole positions or locations, in accordance with various embodiments.

Figure 1:
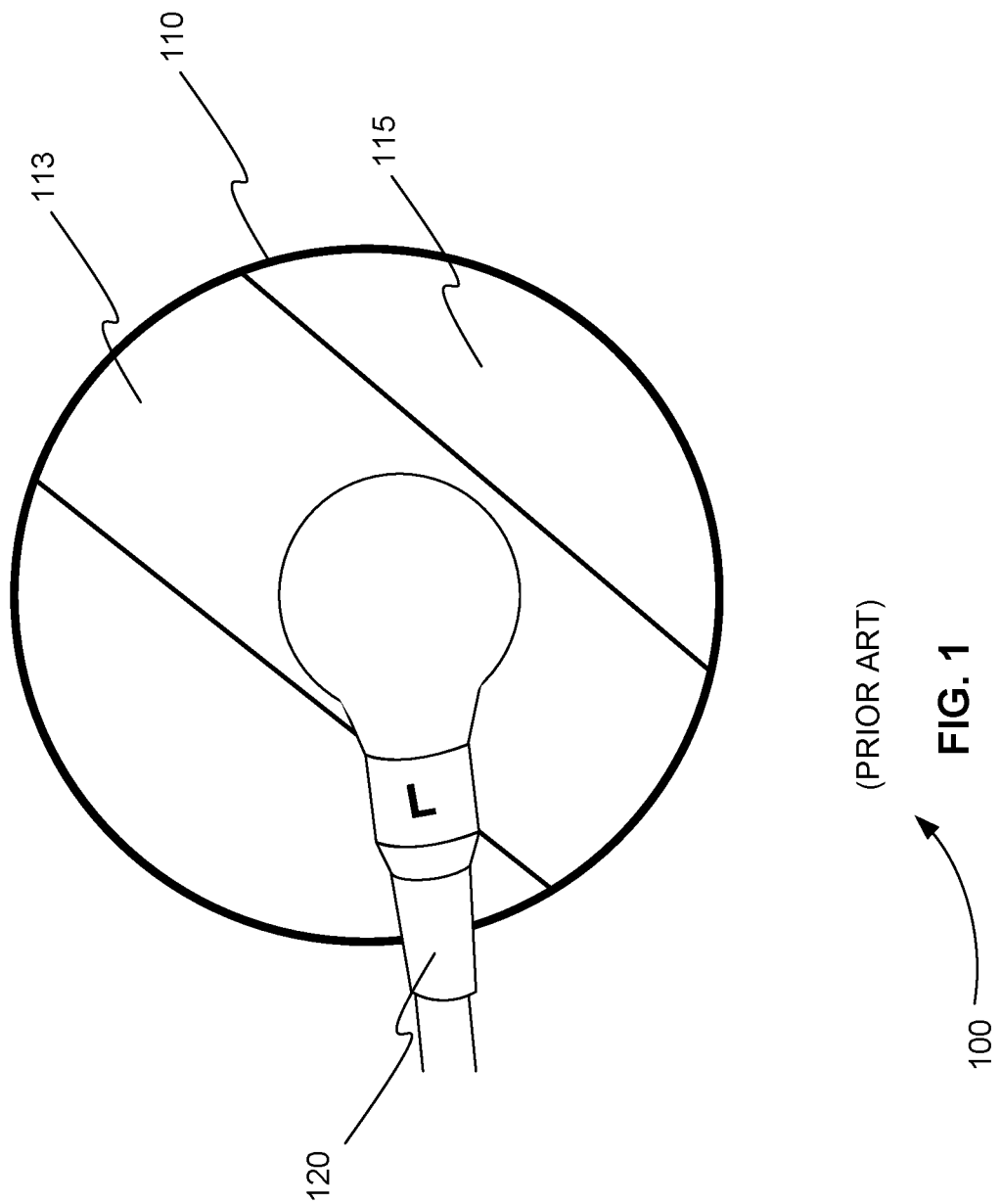
FIG. 1 is a top view of an exemplary snap-type ECG electrode, upon which various embodiments may be implemented.
Figure 2:
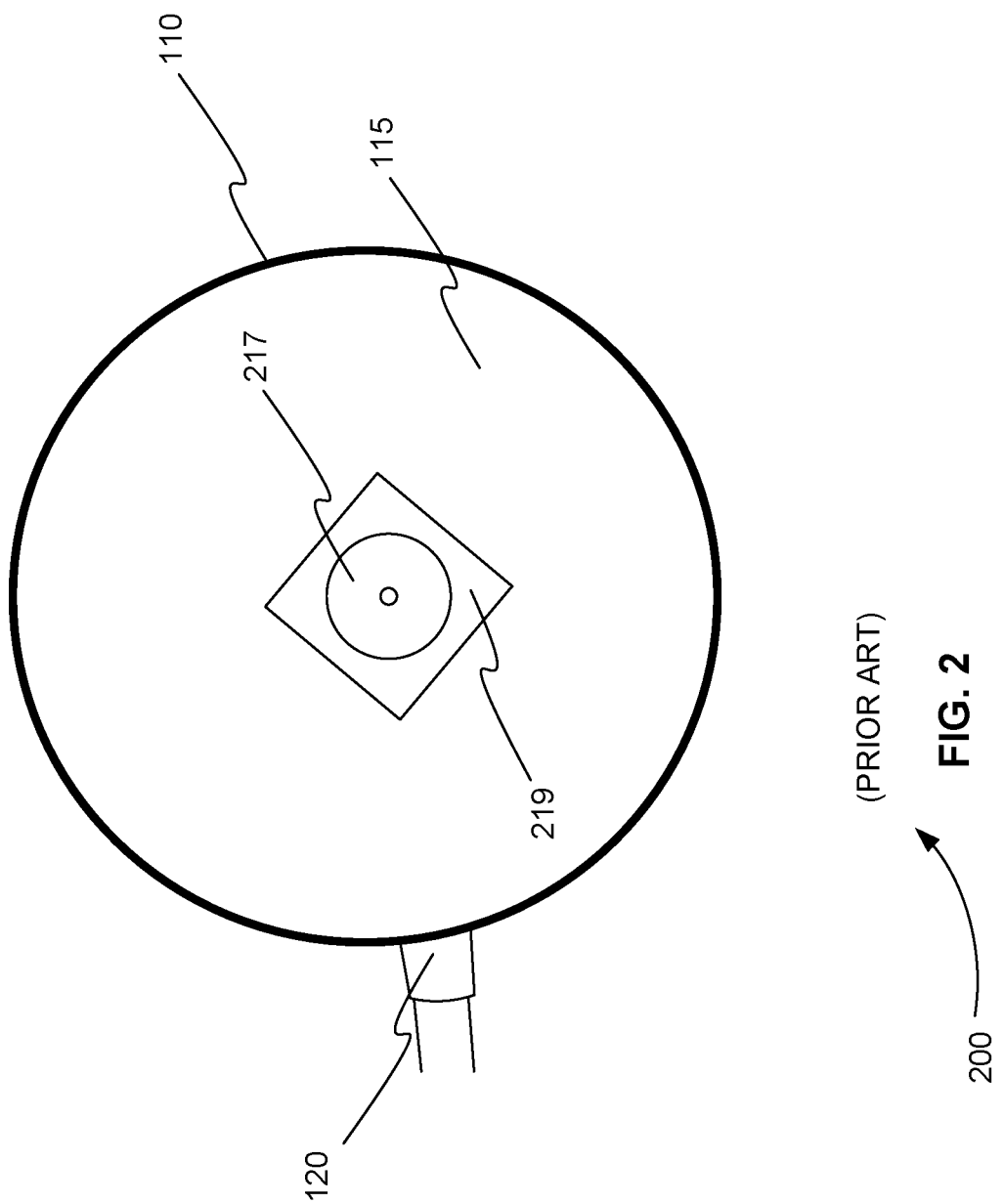
FIG. 2 is a bottom view of an exemplary snap-type ECG electrode, upon which various embodiments may be implemented.
Figure 3:
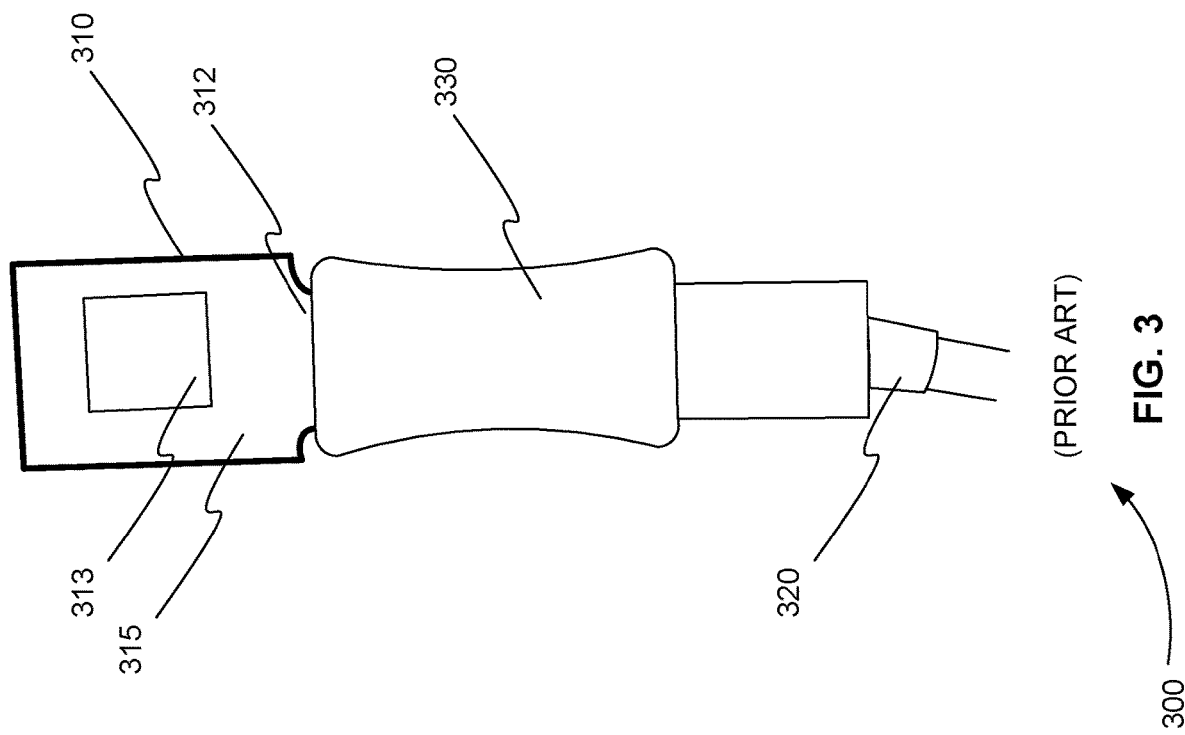
FIG. 3 is a top view of an exemplary tab-type ECG electrode, upon which various embodiments may be implemented.
Figure 4:
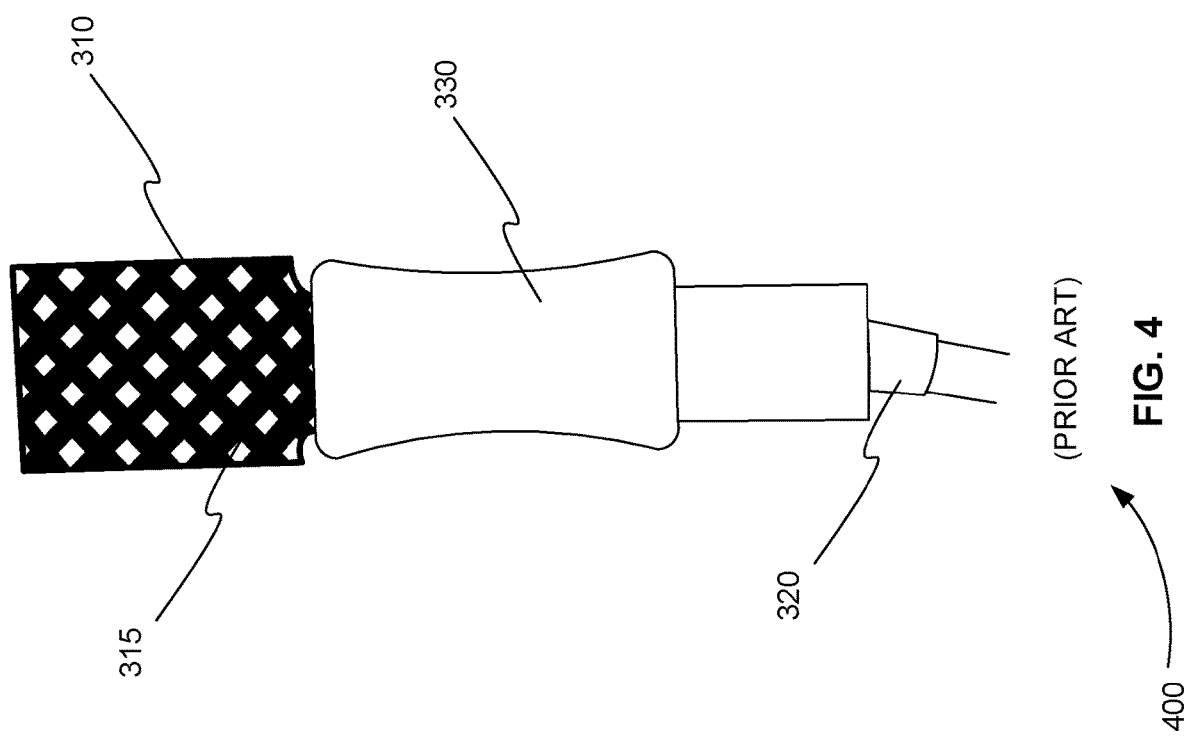
FIG. 4 is a bottom view of an exemplary tab-type ECG electrode, upon which various embodiments may be implemented.

Before one or more embodiments of the invention are described in detail, one skilled in the art will appreciate that the invention is not limited in its application to the details of construction, the arrangements of components, and the arrangement of steps set forth in the following detailed description. The invention is capable of other embodiments and of being practiced or being carried out in various ways. Also, it is to be understood that the phraseology and terminology used herein is for the purpose of description and should not be regarded as limiting.

DETAILED DESCRIPTION

Perforated Disposable ECG Electrodes

As described above, there are two main types of disposable ECG electrodes. The first is the button or snap-type ECG electrode. The second type of disposable ECG electrode is the flat sheet or tab ECG electrode.

To conduct an electrical signal from the skin, both types of electrodes typically include a substrate comprising an Ag to AgCl conductor and an electrolyte gel. To obtain a correct signal from the skin, the electrolyte gel must make and maintain proper contact with the skin. As a result, regions outside of electrolyte gel on the bottom of the substrate further include an adhesive to secure the substrate to the skin. The adhesive and the electrolyte gel can also be mixed on the bottom of the substrate in some embodiments.

Both snap-type and tab-type ECG electrodes have been used for the past century. Unfortunately, however, during this time, both of these types of electrodes have been plagued by adherence problems. Adherence problems for ECG electrodes have been found in the clinic, the hospital setting, and in ECG stress testing. In the clinic, it is been found that ECG electrodes often easily fall off of the body surface. A primary cause of the loosening is a loss of an airtight seal between the electrode and the skin.

In the hospital setting, a primary cause of the electrode coming loose from the surface of the skin is pulling or tearing due to the manipulation of wires and tubes of various other instruments on the patient's body. During exercise or stress testing, a primary cause of the electrode coming loose from the surface of the skin is movement. Exercise movement, daily movement, clothing movement, or various small movements can cause an electrode to be shed or torn off. As a result, a great deal of testing time is lost.

As a result, there is a need for new ECG electrode products and methods of manufacture to allow ECG electrodes to more reliably adhere to the skin and provide a consistent signal to an ECG device over time.

In various embodiments, an ECG electrode product includes one or more holes or vias through the substrate of the ECG electrode that can convey air through the substrate to improve adherence between the substrate of the ECG electrode and the skin of a patient. The ECG electrode product can be a snap-type electrode or a tab-type electrode. The one or more holes can be randomly placed across the substrate or can be symmetrically placed around the substrate.

Figure 5:
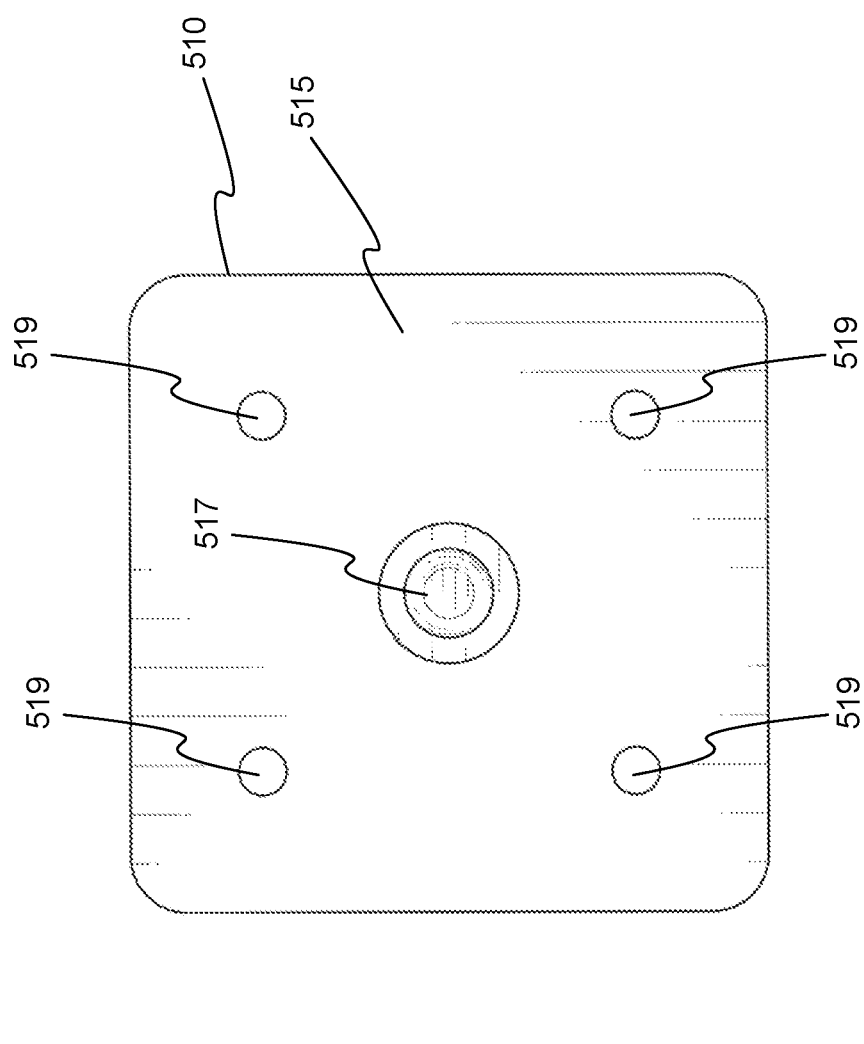
FIG. 5 is an exemplary top view of a square snap-type ECG electrode with four holes, in accordance with various embodiments.

FIG. 5 is an exemplary top view 500 of a square snap-type ECG electrode with four holes, in accordance with various embodiments. Electrode 510 includes male snap 517, substrate 515, and holes 519, which are placed symmetrically around male snap 517.

Figure 6:
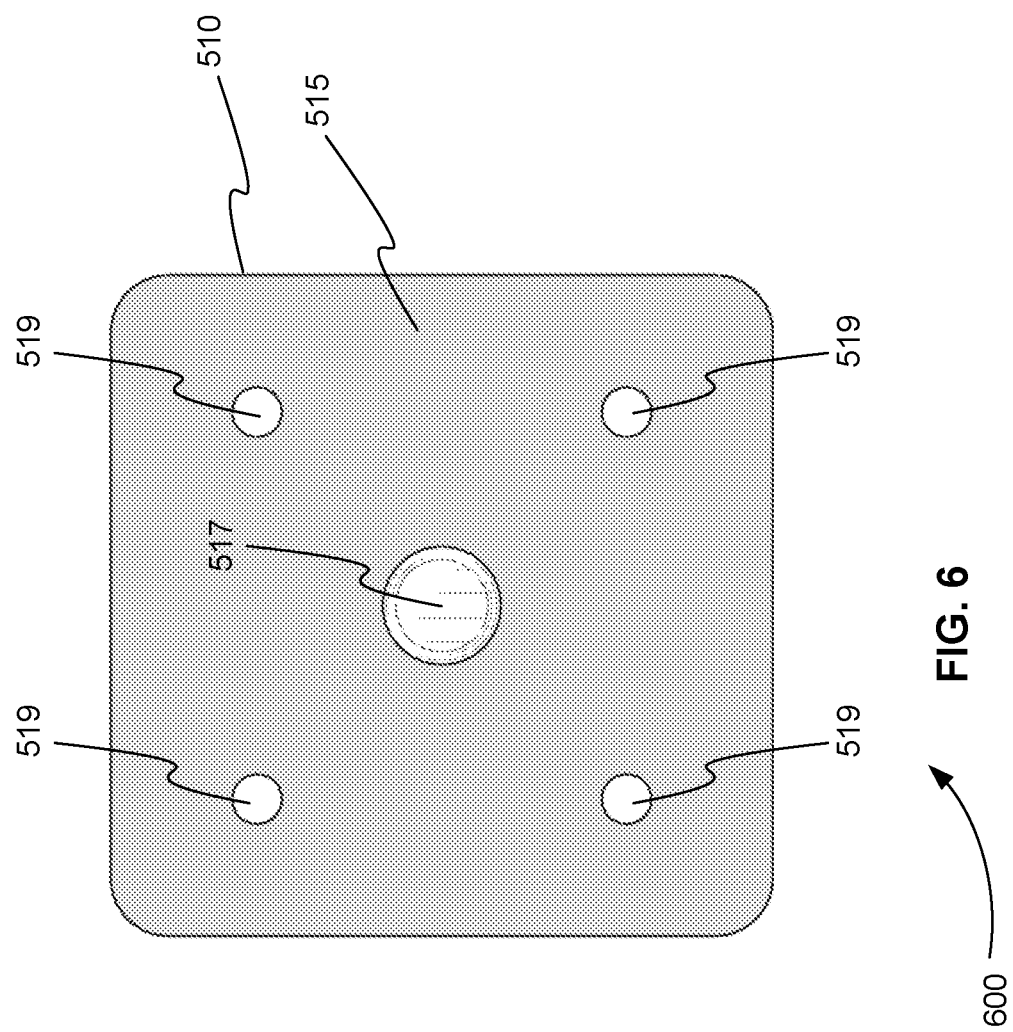
FIG. 6 is an exemplary bottom view of a square snap-type ECG electrode with four holes, in accordance with various embodiments.

FIG. 6 is an exemplary bottom view 600 of a square snap-type ECG electrode with four holes, in accordance with various embodiments. Electrode 510 includes male snap 517, substrate 515, and holes 519, which are placed symmetrically around male snap 517.

Figure 7:
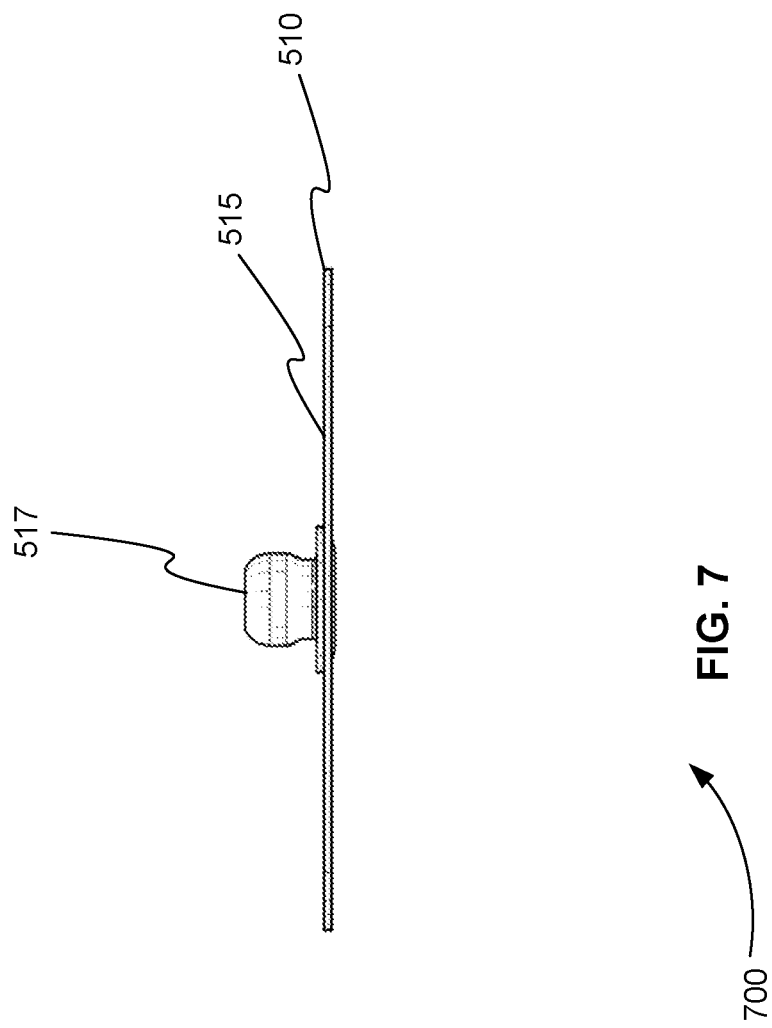
FIG. 7 is an exemplary side view of a square snap-type ECG electrode with four holes, in accordance with various embodiments.

FIG. 7 is an exemplary side view 700 of a square snap-type ECG electrode with four holes, in accordance with various embodiments. Electrode 510 includes male snap 517, substrate 515, and holes (not shown), which are placed symmetrically around male snap 517.

Figure 8:
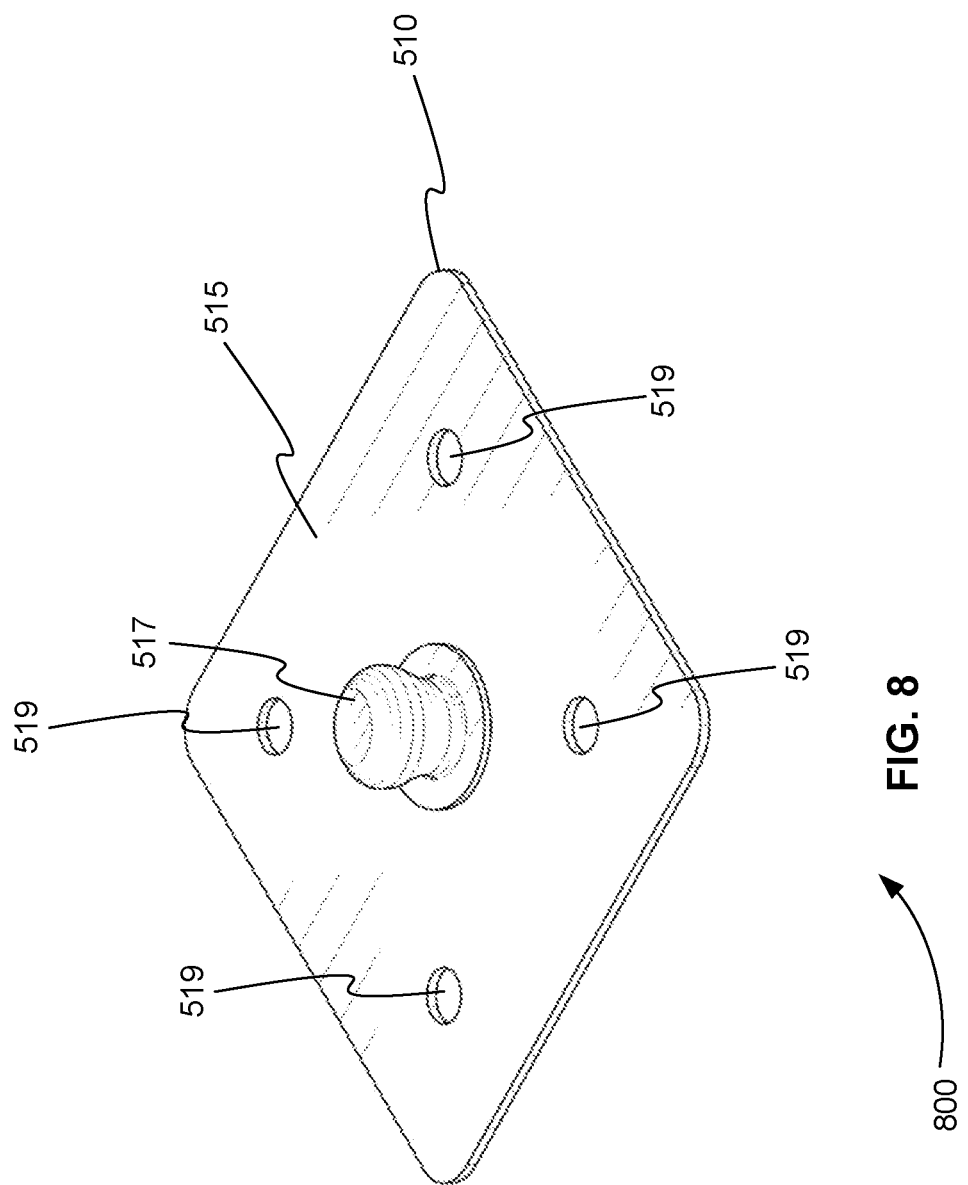
FIG. 8 is an exemplary top perspective view of a square snap-type ECG electrode with four holes, in accordance with various embodiments.

FIG. 8 is an exemplary top perspective view 800 of a square snap-type ECG electrode with four holes, in accordance with various embodiments. Electrode 510 includes male snap 517, substrate 515, and holes 519, which are placed symmetrically around male snap 517.

Figure 9:
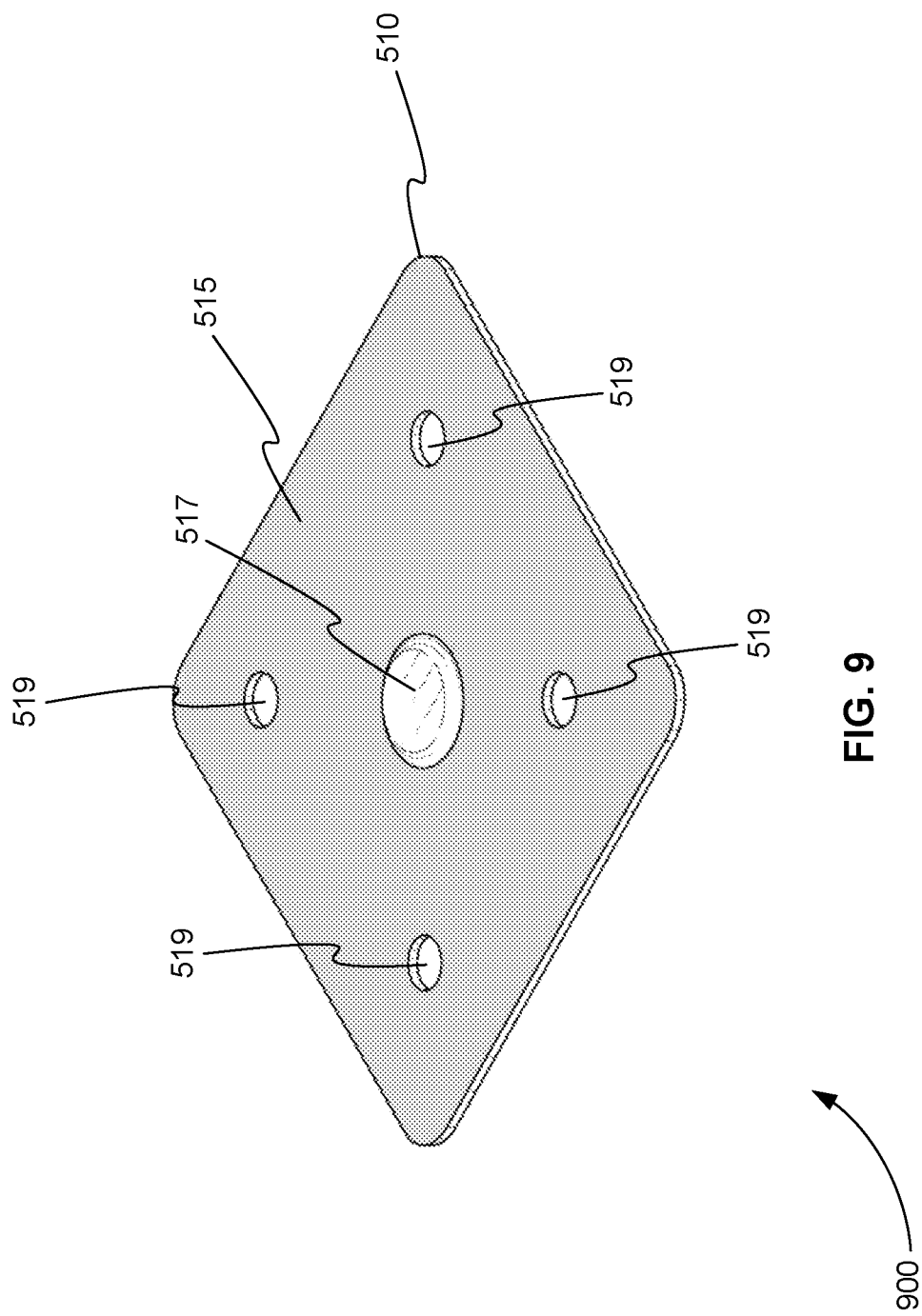
FIG. 9 is an exemplary bottom perspective view of a square snap-type ECG electrode with four holes, in accordance with various embodiments.

FIG. 9 is an exemplary bottom perspective view 900 of a square snap-type ECG electrode with four holes, in accordance with various embodiments. Electrode 510 includes male snap 517, substrate 515, and holes (not shown), which are placed symmetrically around male snap 517.

Figure 10:
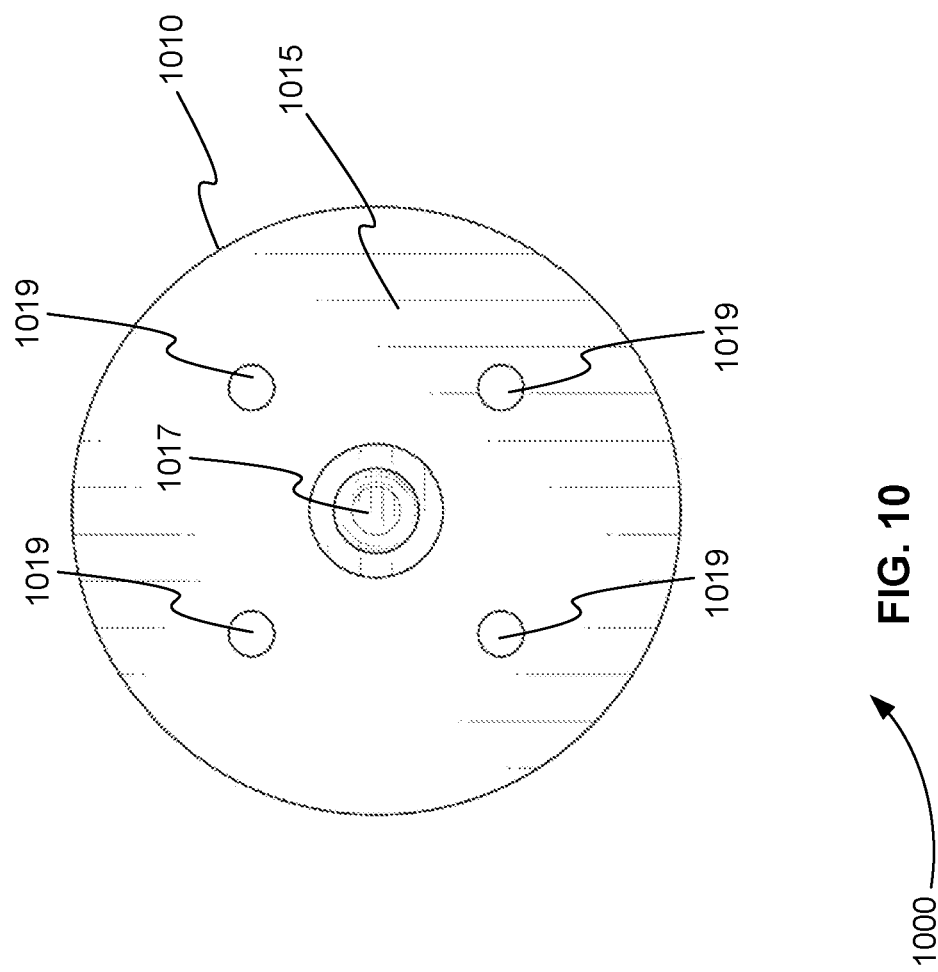
FIG. 10 is an exemplary top view of a circular snap-type ECG electrode with four holes, in accordance with various embodiments.

FIG. 10 is an exemplary top view 1000 of a circular snap-type ECG electrode with four holes, in accordance with various embodiments. Electrode 1010 includes male snap 1017, substrate 1015, and holes 1019, which are placed symmetrically around male snap 1017.

Figure 11:
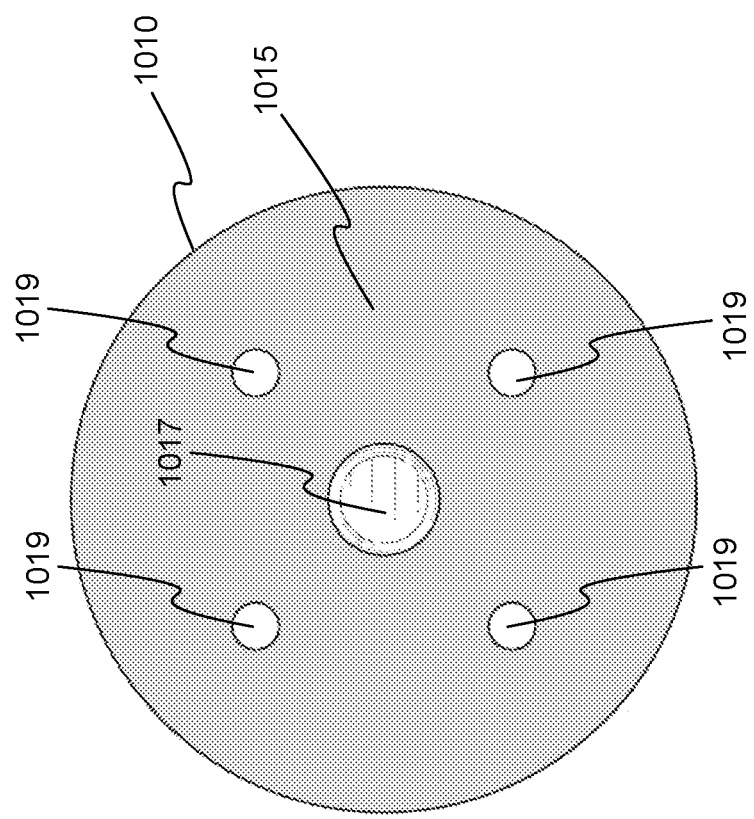
FIG. 11 is an exemplary bottom view of a circular snap-type ECG electrode with four holes, in accordance with various embodiments.

FIG. 11 is an exemplary bottom view 1100 of a circular snap-type ECG electrode with four holes, in accordance with various embodiments. Electrode 1010 includes male snap 1017, substrate 1015, and holes 1019, which are placed symmetrically around male snap 1017.

Figure 12:
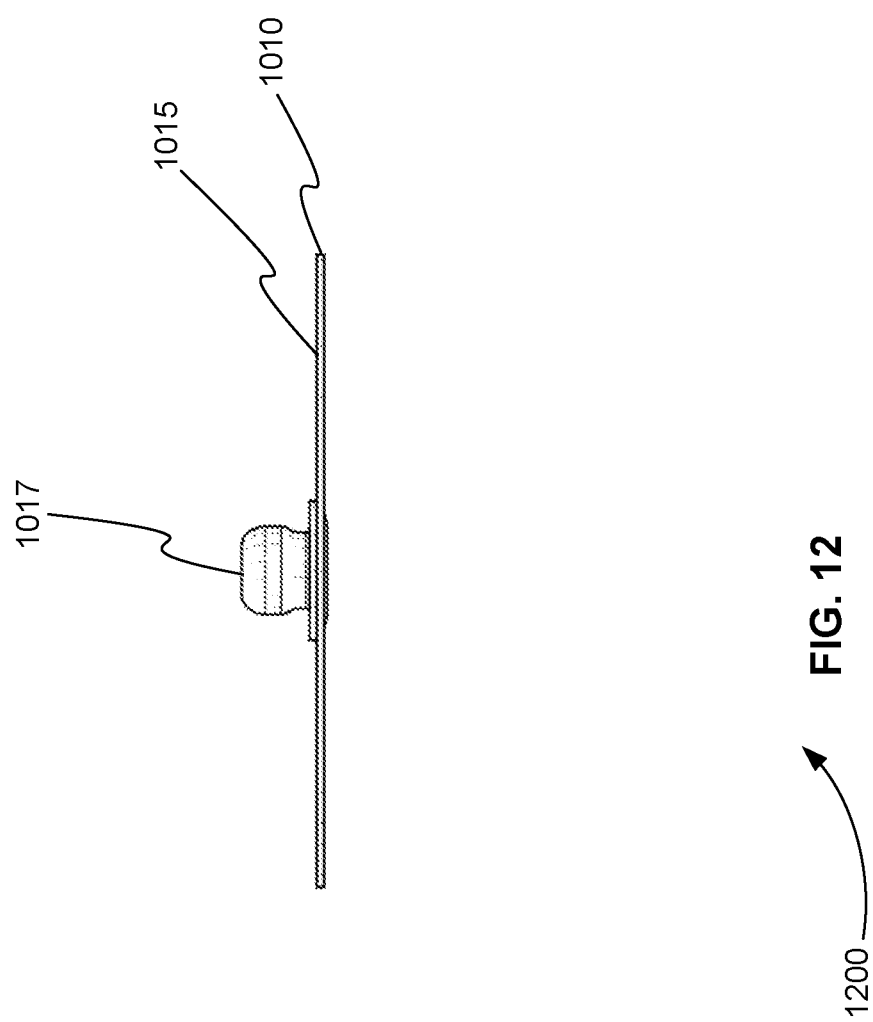
FIG. 12 is an exemplary side view of a circular snap-type ECG electrode with four holes, in accordance with various embodiments.

FIG. 12 is an exemplary side view 1200 of a circular snap-type ECG electrode with four holes, in accordance with various embodiments. Electrode 1010 includes male snap 1017, substrate 1015, and holes (not shown), which are placed symmetrically around male snap 1017.

Figure 13:
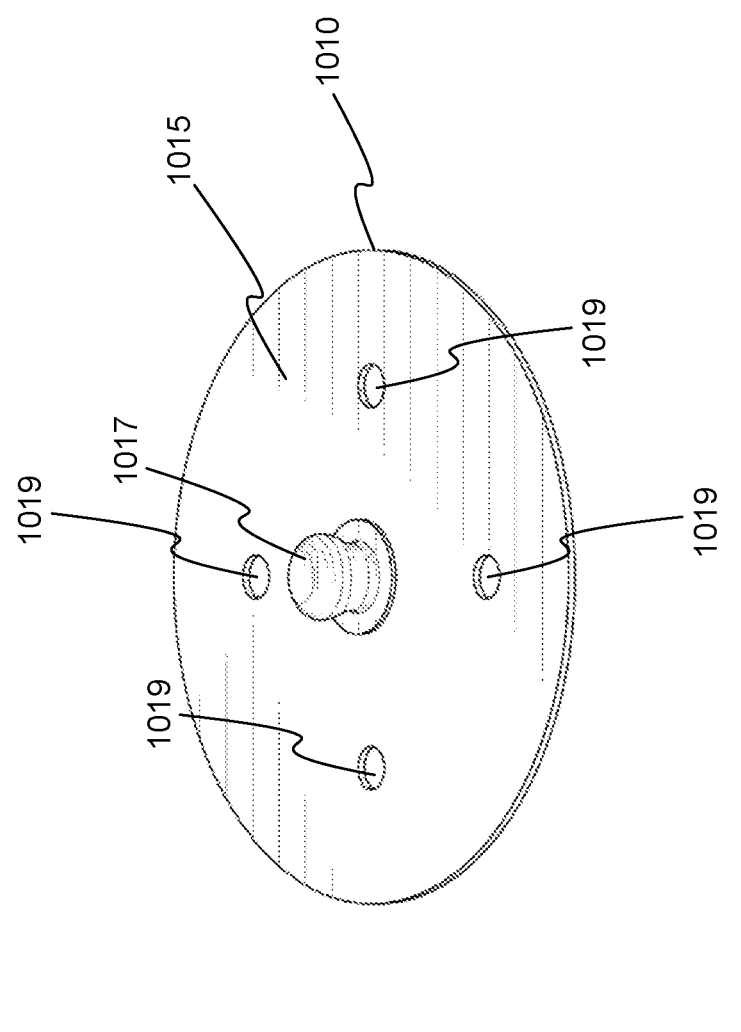
FIG. 13 is an exemplary top perspective view of a circular snap-type ECG electrode with four holes, in accordance with various embodiments.

FIG. 13 is an exemplary top perspective view 1300 of a circular snap-type ECG electrode with four holes, in accordance with various embodiments. Electrode 1010 includes male snap 1017, substrate 1015, and holes 1019, which are placed symmetrically around male snap 1017.

Figure 14:
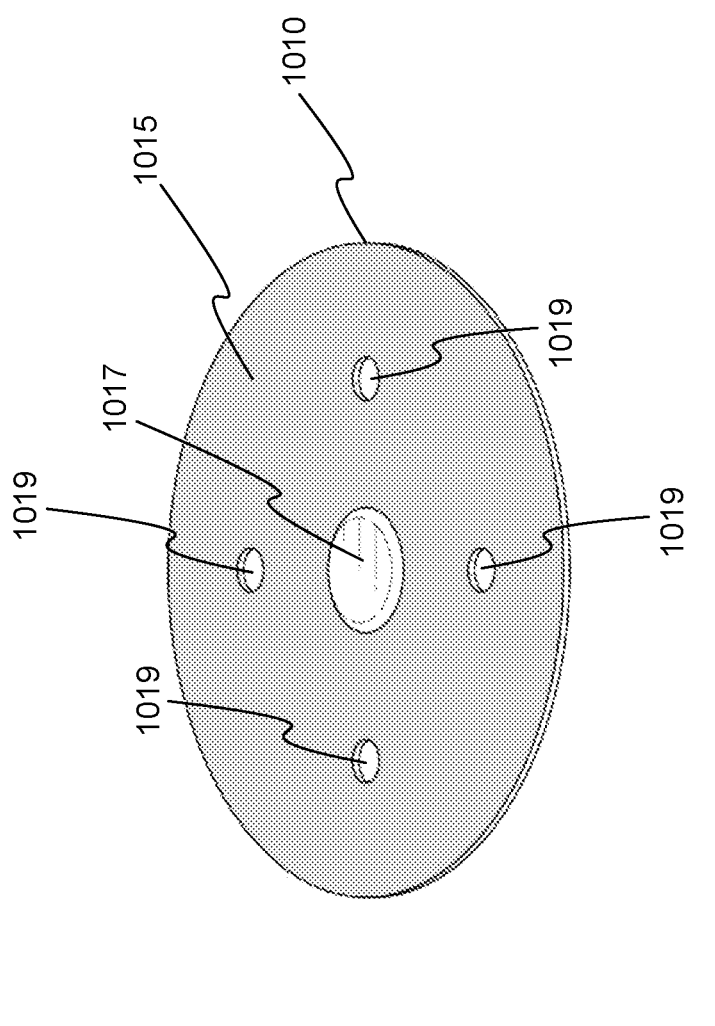
FIG. 14 is an exemplary bottom perspective view of a circular snap-type ECG electrode with four holes, in accordance with various embodiments.

FIG. 14 is an exemplary bottom perspective view 1400 of a circular snap-type ECG electrode with four holes, in accordance with various embodiments. Electrode 1010 includes male snap 1017, substrate 1015, and holes (not shown), which are placed symmetrically around male snap 1017.

In various embodiments, a method of manufacture of an ECG electrode includes perforating one or more holes in a substrate of an ECG electrode that can convey air through the substrate to improve adherence between the substrate of the ECG electrode and the skin of a patient. In various embodiments, the one or more holes are made after the substrate is sealed. In various alternative embodiments, the one or more holes are made before the substrate and all of its layers are sealed.

In various embodiments, the shape of the one or more holes can be customized. The shape can include, but is not limited to, a circle, square, star, triangle, or polygon.

Figure 15:
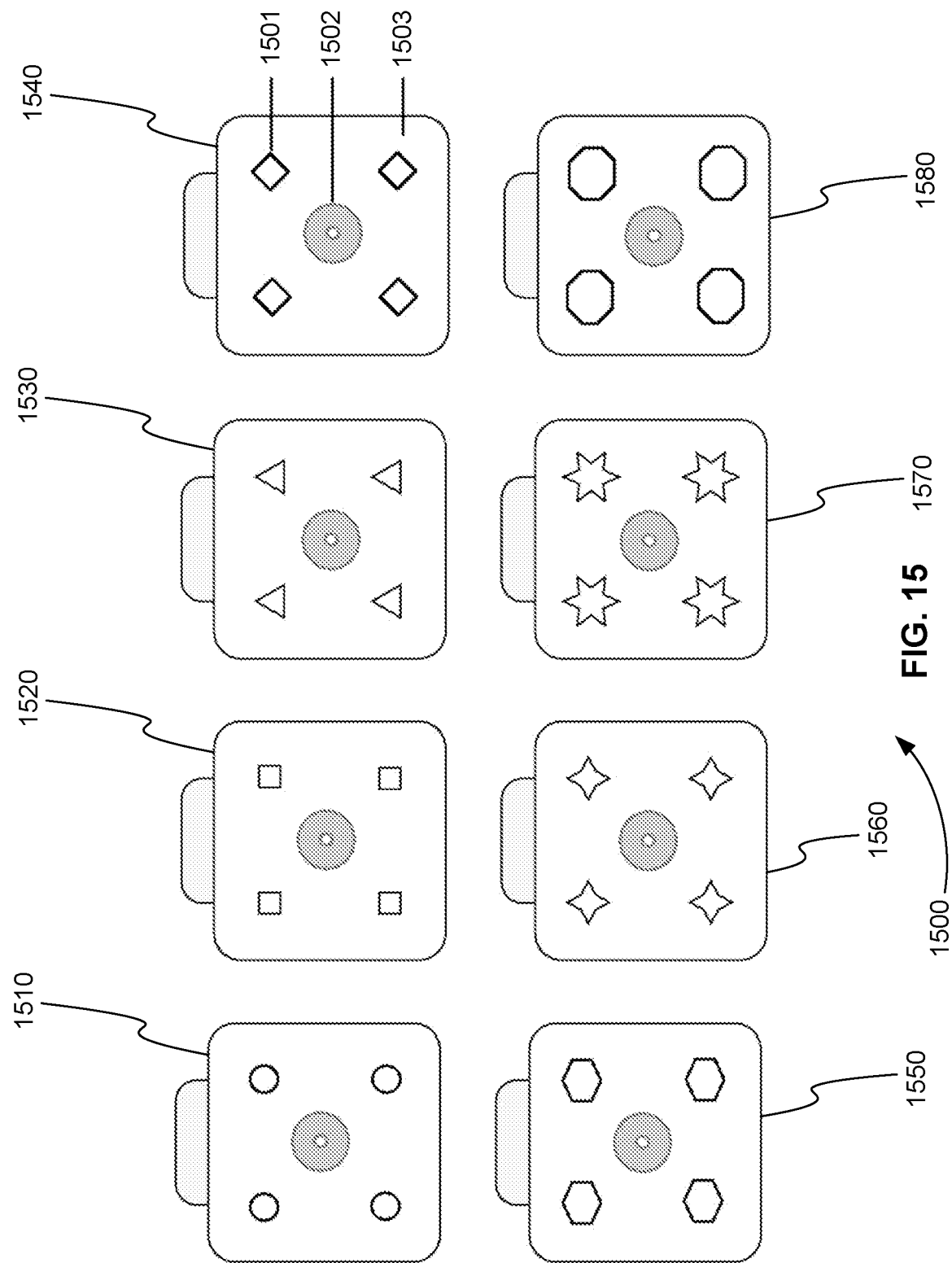
FIG. 15 is an exemplary diagram showing top views of eight different square snap-type ECG electrodes with different hole shapes, in accordance with various embodiments.

FIG. 15 is an exemplary diagram 1500 showing top views of eight different square snap-type ECG electrodes with different hole shapes, in accordance with various embodiments. Electrodes 1510, 1520, 1530, and 1540 include circular, rectangular, triangular, and diamond-shaped holes, respectively. Electrodes 1550 and 1580 include six and eight-sided polygon-shaped holes, respectively. Electrodes 1560 and 1570 include four and six-pointed star-shaped holes, respectively. Each of electrodes 1510-1580 includes four holes 1501, a male snap 1502, and a substrate 1503.

In various embodiments, electrodes with different shaped holes may be used for different patients or different applications. For example, electrodes 1550-1580 can be used for patients with hairy chests and arms. The holes of these electrodes enhance the adhesion of the electrode, reduce a bottom gap caused by hair, and provide multiple edges in each hole that can resist shedding caused by hair. In contrast, electrodes 1510-1540 can be used for patients with smooth skin or less hair.

Conventionally the traditional shape of an electrode substrate is round, square, or oval, for example. Ideally is makes a tight seal with the skin at the bottom of the electrode, completely isolated from the air. As described above, however, the problem is that the electrode often falls off, because the non-toxic and biocompatible glue is not sticky enough, hair interferes with the adhesion, or the movement of the electrode or lead wire tears the electrode away from the skin.

In various embodiments, one or more holes in the substrate of the electrode provide a vent allowing air through a limited area of the electrode. and the air. These holes (35 to 55 mm wide, for example) provide via holes or columns for air within the electrode. These columns make it more difficult to move the electrode horizontally and vertically and achieve improved tensile strength to prevent tearing and pulling.

In a conventional electrode, the gripping surface is one smooth plane. In contrast, in various embodiments, the holes of different shapes in an electrode communicate with the outside world and obtain multiple grasping points. The conventional electrode has only one side, but an electrode of various embodiments has many points on one side. The surface of the conventional electrode is isolated from the air, while an electrode of various embodiments includes one or more holes that allow air penetration. In general, the one or more holes of an electrode of various embodiments help prevent the electrode from moving or falling off and from being pulled off or torn by external forces. Therefore, the tensile strength and anti-shedding function of an electrode of various embodiments are increased.

In various embodiments, an electrode with a circular shape is more suitable for a patient with a greater volume size, whereas a square electrode is more suitable for a thinner patient with less volume. Oval electrodes have a very wide chest (the force on the long edge is stronger than that on the short edge). The tensile strength is increased by adding holes with multiple edges in the area of round, square, and ellipse electrodes. If these different types of holes are used, the adhesion strength can be increased.

In various embodiments, the position the one or more holes can be fixed or random. In addition, as described below, the position can be determined using artificial intelligence (AI).

FIG. 16 is an exemplary diagram 1600 showing top views of four different tab-type ECG electrodes with different hole positions or locations, in accordance with various embodiments. Electrodes 1610 and 1620 include four holes 1601 positioned symmetrically and uniformly around these electrodes. Electrode 1630 includes 12 holes 1631 positioned uniformly around the electrode. Electrode 1640 includes 10 holes 1641 positioned randomly around the electrode.

In various embodiments, the shapes of holes in one electrode can be varied.

Figure 17:
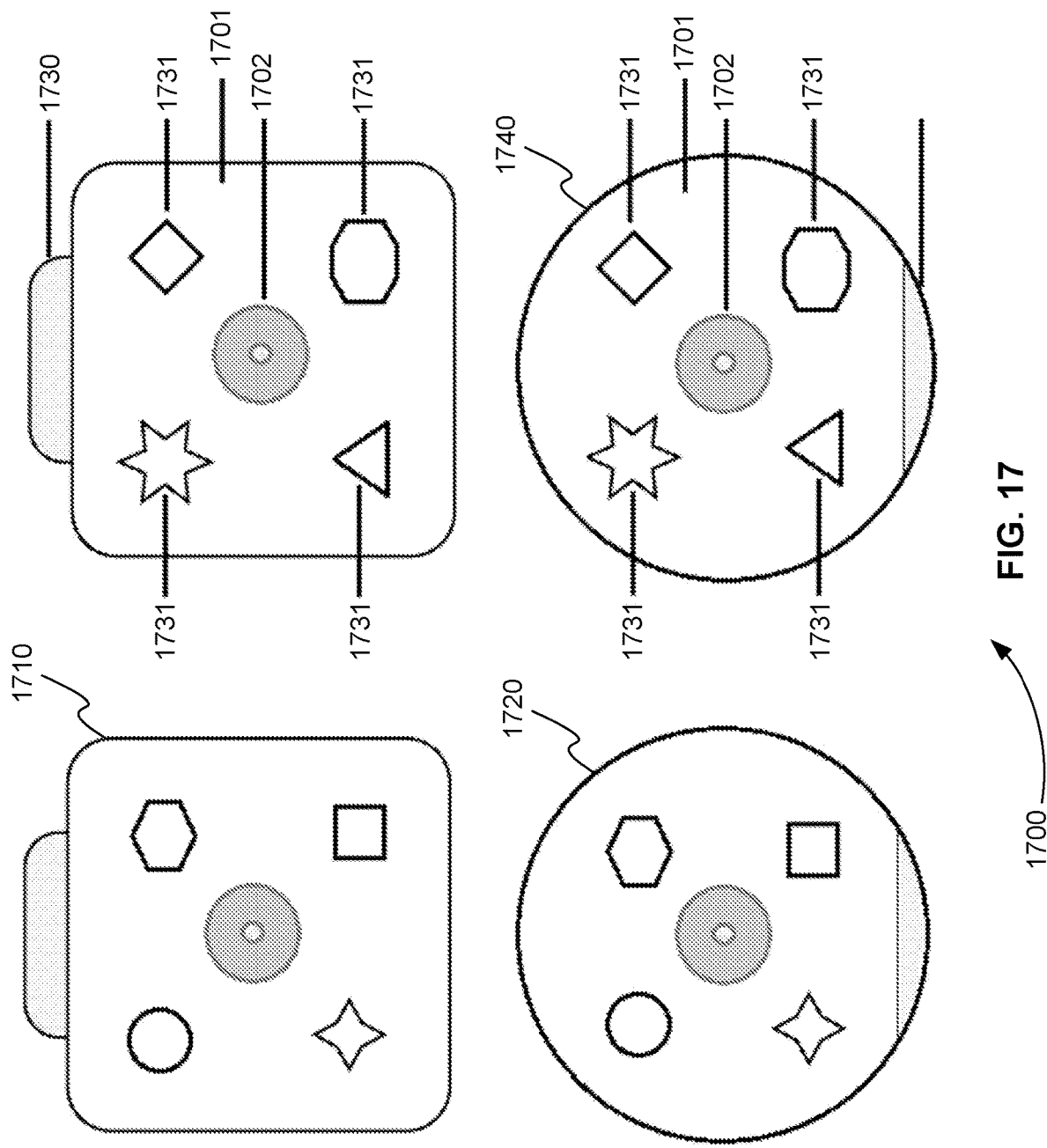
FIG. 17 is an exemplary diagram showing top views of four snap-type ECG electrodes that each have holes with different shapes, in accordance with various embodiments.

FIG. 17 is an exemplary diagram 1700 showing top views of four snap-type ECG electrodes that each have holes with different shapes, in accordance with various embodiments. Electrodes 1710 and 1720 are square and circular snap-type ECG electrodes, respectively, with a first set of four holes with different shapes. Electrodes 1730 and 1740 are square and circular snap-type ECG electrodes, respectively, with a second different set of four holes 1731 with different shapes. Electrodes 1710-1740 include a substrate 1701 and male snap 1702.

In various embodiments, after all the holes are made on an electrode substrate, the holes penetrate through the electrode and penetrate to the skin surface, which is similar to adding several independent but connected electrodes. This allows the adhesion of the electrode to be improved without changing the composition of the adhesive or the colloid (electrolyte gel) of the electrode.

The conventional electrode does not include holes to prevent shedding. The contact layer between the conventional electrode and the skin is one an airtight seal. When the external tension of the lead wire is encountered, the whole electrode surface more easily falls off, because the sealed electrode has only one surface and no additional binding point.

Artificial Intelligence for Electrode Shape

As described above, how to improve the performance of an electrode without changing the composition of the adhesive has been a challenge in the industry. In various embodiments, artificial intelligence (AI) is used to determine the shape of an electrode to obtain the best adhesion force and tensile strength, as well as to detect subtle electrical signals.

In various embodiments, the best electrode shape is selected from a calculation. If the periphery of the electrode (or shape of the electrode substrate) is octagonal, an oval hole or a crescent hole is made in the electrode, which is more suitable for the asymmetric area. This ensures a longer boundary of the electrode and avoids a very wide colloidal area, to provide better adhesion and tension resistance.

Figure 18:
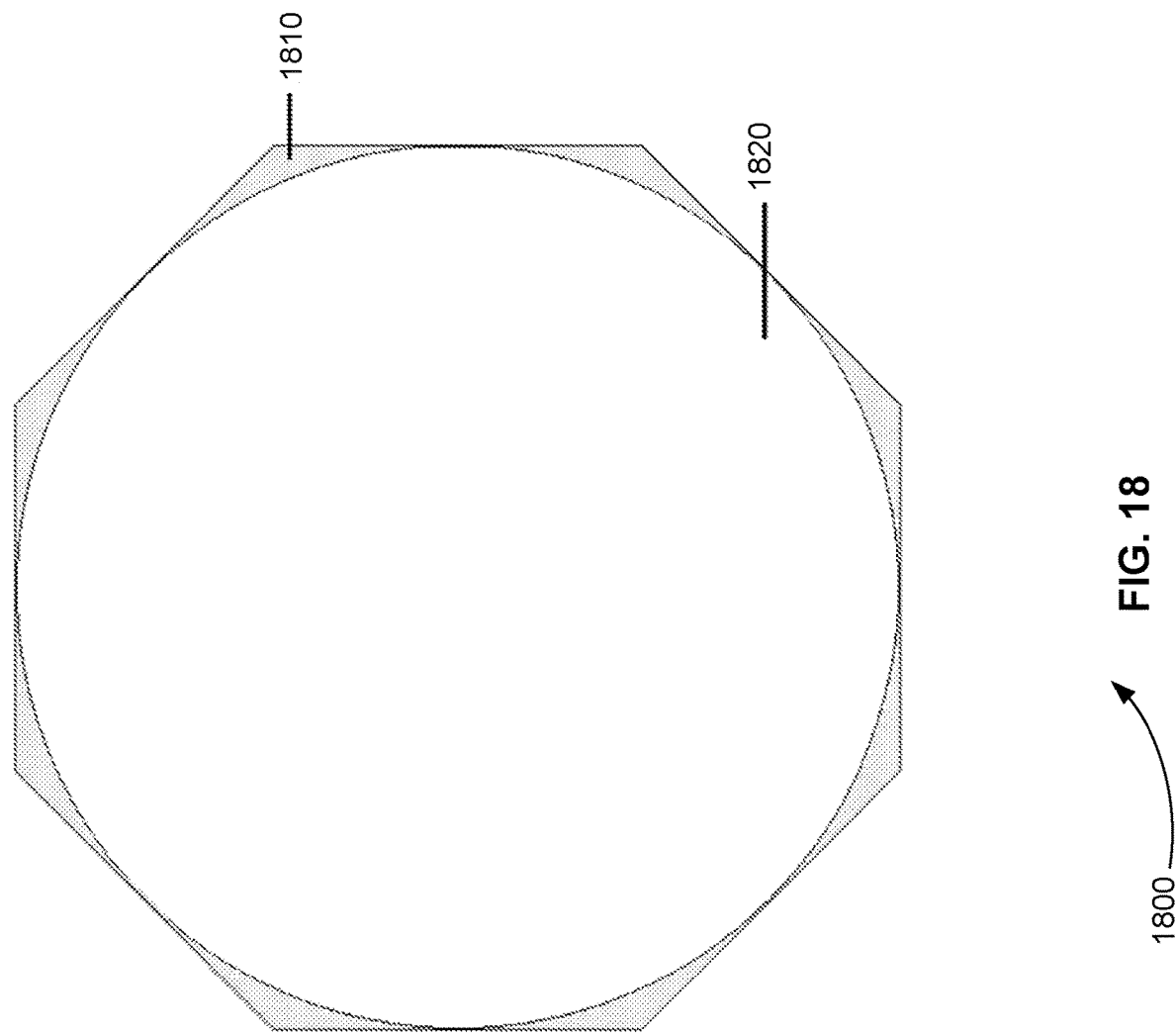
FIG. 18 is an exemplary diagram 1800 showing the shape of an ECG electrode substrate calculated by AI to provide better adhesion and tension resistance, in accordance with various embodiments.

FIG. 18 is an exemplary diagram 1800 showing the shape of an ECG electrode substrate calculated by AI to provide better adhesion and tension resistance, in accordance with various embodiments. Octagonal shape 1810 provides better adhesion and tension resistance over the conventional circular shape 1820, for example. Circular shape 1820 is shown within octagonal shape 1810 for comparison only. The greater adhesion force and tensile strength achieves the effect of anti-shedding.

If the electrode shape is circular or round, it has one edge only. If it is crescent-shaped, the edge has only two sides. If it is square, the edge has only four sides. If it is octagonal, the enclosed figure formed by the eight line edges connected end to end has eight angles. Octagons can be divided into regular octagonal and non-octagonal. Equal angles and equal lengths are gathered in an octagon. An octagonal shape has 8-sides, and the sum of inner and outer angles is 360 degrees. If the diameter of the "8-angle" electrode is the same as that of the "circular" electrode, referring to FIG. 18, it can be seen that there are eight external angles outside the circle, which increases the adhesion force, and each angle has its own adhesion force. The circular electrode has only one edge at the outer corner of 360 degrees. Eight edges and eight angles are added to the 8-angle electrode.

The advantage of AI is that it can create any graph determined by a formula, including all shapes and various types of holes, and can also change all angles into a certain radian to produce the various shapes. This can produce an electrode with better adhesion and the strongest anti-shedding ability.

In various embodiments, the design of the electrode also includes the design of one or more holes of the electrode. These holes can be made with different shapes, as described above. For example, the holes can be regular octagonal, specific octagonal, circular, elliptical, or hexagonal.

In various embodiments, four or more oval holes are used. Four elliptical holes are made near the edge of an electrode sheet at ⅓ of the circumference diameter. The positions of the four elliptical holes are not horizontally symmetrical but symmetrical with four edges of the eight corners, the middle four holes are oval-like building columns, and the longest edge of the ellipse is arranged around the center of the metal buckle of the electrode lead. There are two parameters for AI optimization of elliptical holes: the ratio of long shape to short shape, and 180-degree selection of ellipse orientation. The shape of the electrode can be round or hexagonal. The four holes are made to be four ellipses around the center, which fix the metal snap closer to the skin. In addition, the holes help gather the signals more in the center, to collect more delicate electrical signals.

Figure 19:
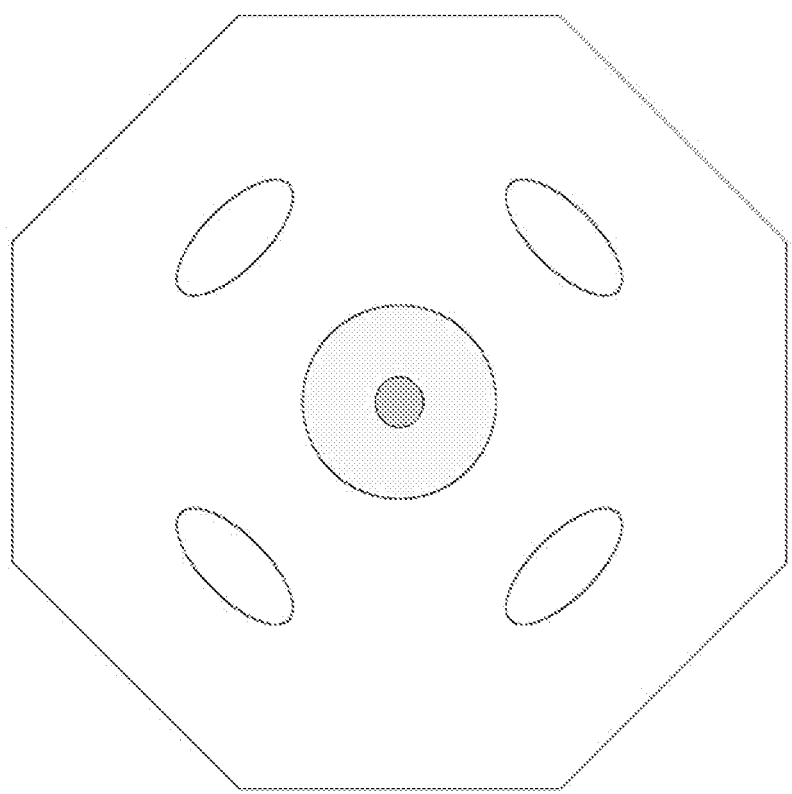
FIG. 19 is an exemplary diagram showing a bottom view of a hexagonally shaped snap-type ECG electrode with four elliptical holes around the center of the electrode calculated by AI to provide better adhesion and tension resistance, in accordance with various embodiments.

FIG. 19 is an exemplary diagram 1900 showing a bottom view of a hexagonally shaped snap-type ECG electrode with four elliptical holes around the center of the electrode calculated by AI to provide better adhesion and tension resistance, in accordance with various embodiments.

In various embodiments, four crescent-shaped holes are made at the edge of four corners in the circumference of ⅓ of the inner and outer edge of an electrode. The crescent-shaped holes have a long edge (convex surface) and a short edge (concave surface). The concave surface fixes the conductive angle in an area, which is more concentrated to the field potential, and has a stronger anti-shedding and pulling function and effect.

Figure 20:
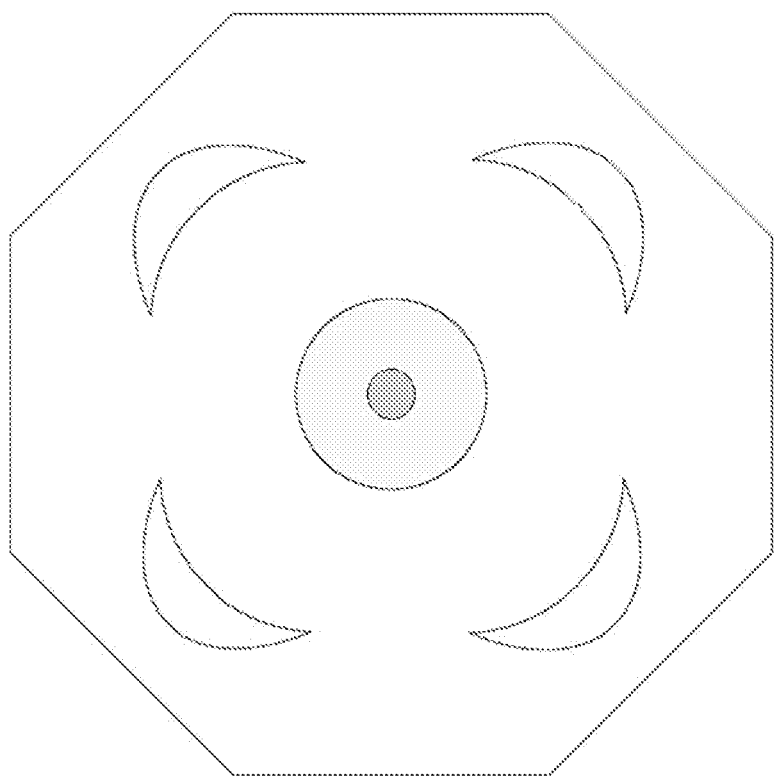
FIG. 20 is an exemplary diagram showing a bottom view of a hexagonally shaped snap-type ECG electrode with four crescent-shaped holes around the center of the electrode calculated by AI to provide better adhesion and tension resistance, in accordance with various embodiments.

FIG. 20 is an exemplary diagram 2000 showing a bottom view of a hexagonally shaped snap-type ECG electrode with four crescent-shaped holes around the center of the electrode calculated by AI to provide better adhesion and tension resistance, in accordance with various embodiments.

In various embodiments, pairs of symmetrical crescent-shaped holes are made at four corners within ⅓ of the circumference inside and outside of an electrode. The long edge is in the outward force; the short edge is in the inward force. This shape can achieve better results for the thinner patients or the elderly, due to less muscle under the skin and fewer signal sources.

Figure 21:
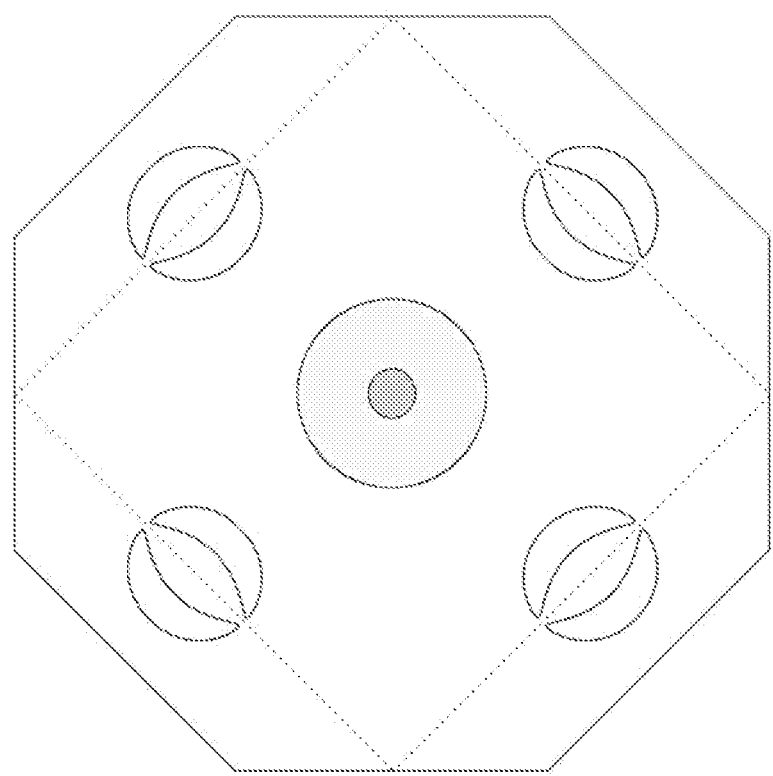
FIG. 21 is an exemplary diagram showing a bottom view of a hexagonally shaped snap-type ECG electrode with four pairs of crescent-shaped holes around the center of the electrode calculated by AI to provide better adhesion and tension resistance, in accordance with various embodiments.

FIG. 21 is an exemplary diagram 2100 showing a bottom view of a hexagonally shaped snap-type ECG electrode with four pairs of crescent-shaped holes around the center of the electrode calculated by AI to provide better adhesion and tension resistance, in accordance with various embodiments.

In various embodiments, two symmetrical non-angular elliptical holes are made on the left and right sides of an electrode. The two large ellipses can gather and expose the hair in the oval hole. This is specially designed for the hairy patient. It has an anti-hair effect.

Figure 22:
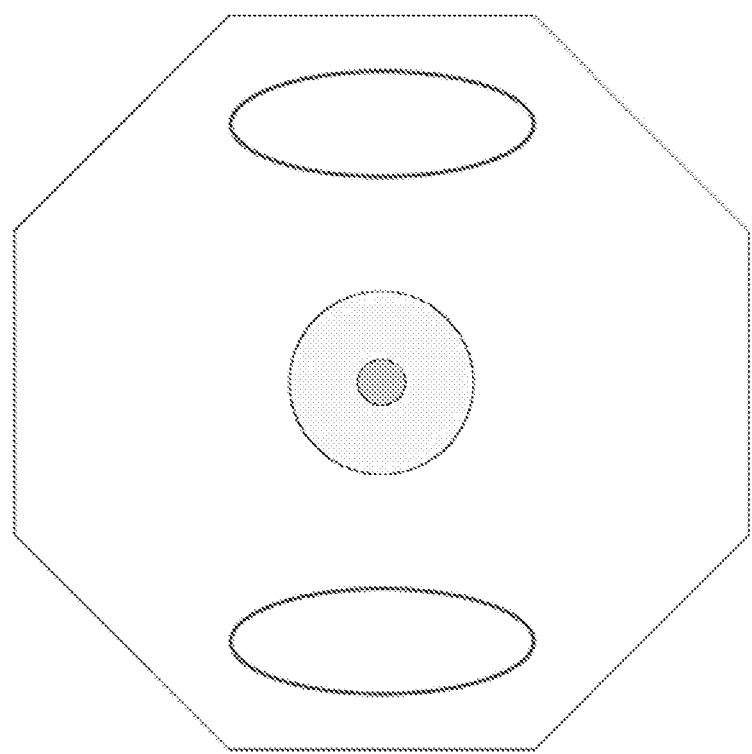
FIG. 22 is an exemplary diagram showing a bottom view of a hexagonally shaped snap-type ECG electrode with two symmetrical non-angular elliptical holes on either side of the center of the electrode calculated by AI to provide better adhesion and tension resistance, in accordance with various embodiments.

FIG. 22 is an exemplary diagram 2200 showing a bottom view of a hexagonally shaped snap-type ECG electrode with two symmetrical non-angular elliptical holes on either side of the center of the electrode calculated by AI to provide better adhesion and tension resistance, in accordance with various embodiments.

In various embodiments, four round or square holes are made in an electrode. The holes are closely arranged around the center of the metal snap of the electrode. The adhesive force between point and surface is increased. It has stronger anti-shedding. Tests show that this design can obtain clearer and more detailed electrical signals.

Figure 23:
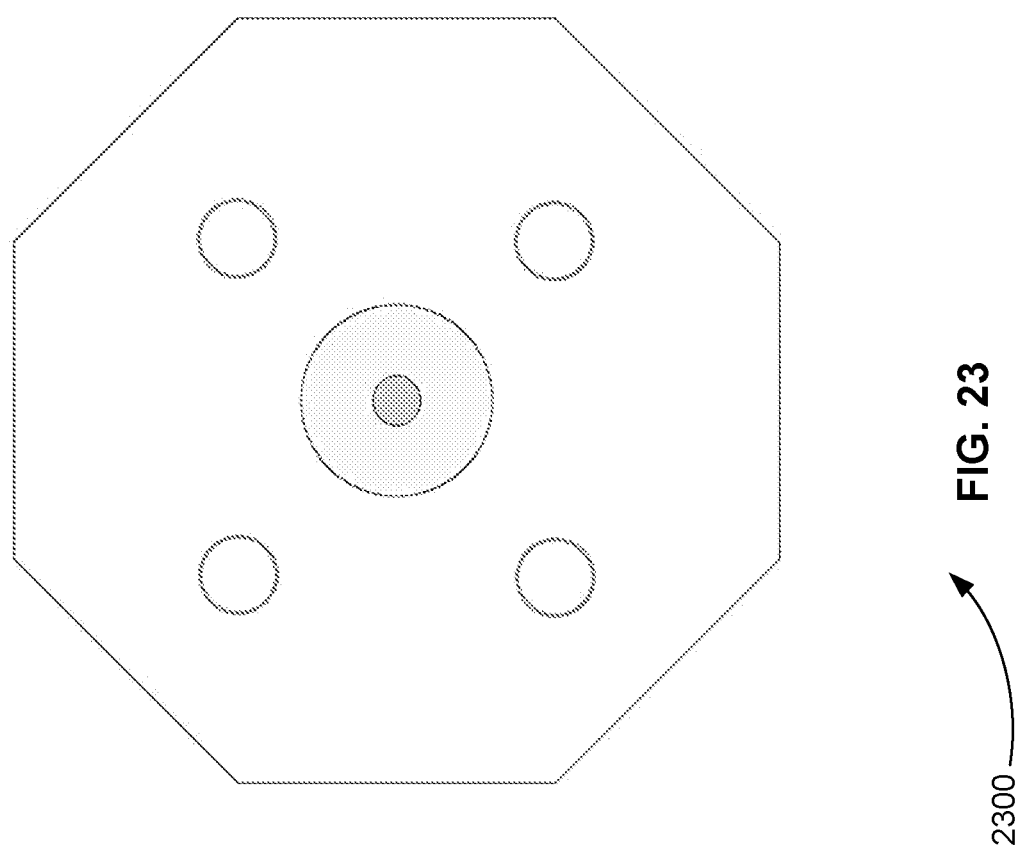
FIG. 23 is an exemplary diagram showing a bottom view of a hexagonally shaped snap-type ECG electrode with four circular holes made around the center of the electrode calculated by AI to provide better adhesion and tension resistance, in accordance with various embodiments.

FIG. 23 is an exemplary diagram 2300 showing a bottom view of a hexagonally shaped snap-type ECG electrode with four circular holes made around the center of the electrode calculated by AI to provide better adhesion and tension resistance, in accordance with various embodiments.

In various embodiments, a fractal electrode shape is used. The shape is based on a circle. After calculation, it is found that on the basis of the outer circle, five similar semicircles are added on the edge. After the semicircle is added with the edge, the strength of adhesion and tensile is increased compared with the circle. Five holes are made around the center metal snap of the electrode.

Figure 24:
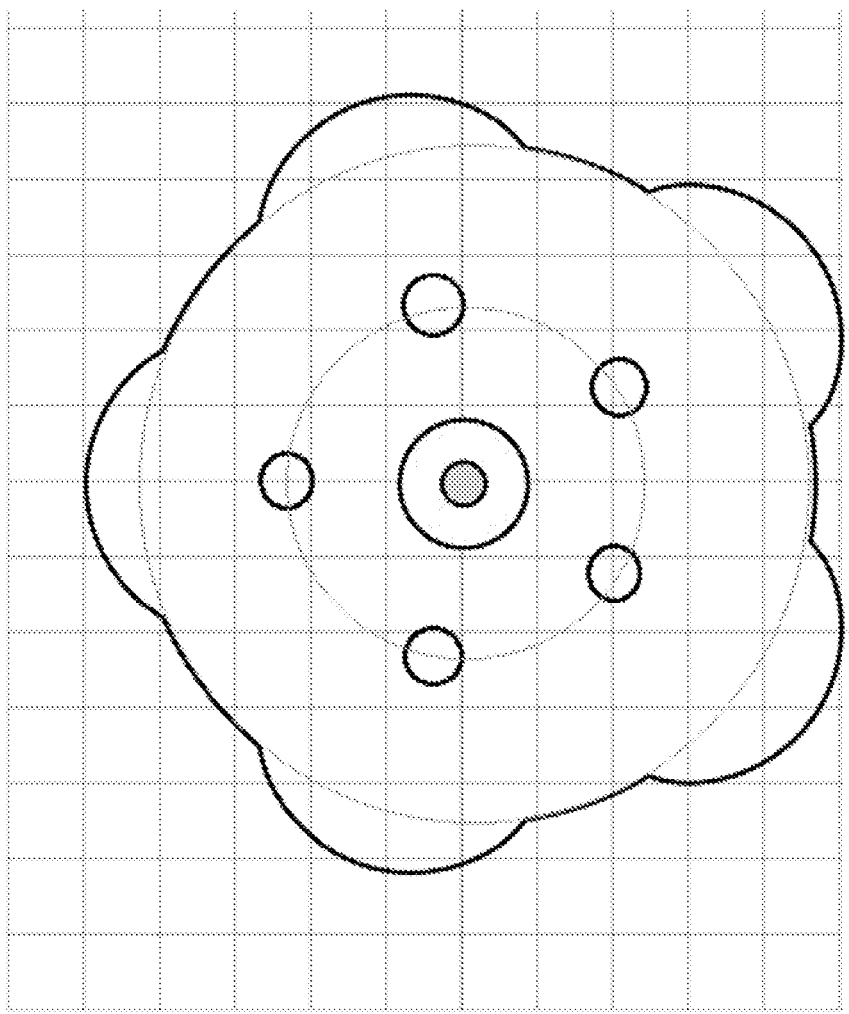
FIG. 24 is an exemplary diagram showing a bottom view of a circular-shaped snap-type ECG electrode with five semicircular edges and five circular holes made around the center of the electrode calculated by AI to provide better adhesion and tension resistance, in accordance with various embodiments.

FIG. 24 is an exemplary diagram 2400 showing a bottom view of a fractal circular-shaped snap-type ECG electrode with five semicircular edges and five circular holes made around the center of the electrode calculated by AI to provide better adhesion and tension resistance, in accordance with various embodiments.

ECG Electrode with Holes

Returning to FIG. 14, ECG electrode 1010 includes substrate 1015 and one or more holes 1019. Substrate 1015 includes on one side an electrolyte gel for contacting a patient's skin and an adhesive. One or more holes 1019 perforate substrate 1015 and the adhesive to increase the adhesion between the patient's skin and substrate 1015.

In various embodiments, ECG electrode 1010 is a snap-type electrode, as shown in FIG. 14. In various alternative embodiments, ECG electrode 1010 is a tab-type electrode.

In various embodiments, substrate 1015 has a circular shape, as shown in FIG. 14.

In various embodiments, substrate 1015 has a rectangular shape, as shown in FIG. 9.

In various embodiments, substrate 1015 has a hexagonal shape, as shown in FIG. 19.

In various embodiments, substrate 1015 has a circular shape with one or more semicircular edges equally spaced along the edge of the circular shape, as shown in FIG. 24.

In various embodiments, one or more holes 1019 include four holes symmetrically positioned on the substrate, as shown in FIG. 14.

In various embodiments, one or more holes 1019 are symmetrically positioned around snap 1017 of the snap-type electrode 1010, as shown in FIG. 14.

In various embodiments, one or more holes 1019 one or more of a circular shape, rectangular shape, crescent shape, polygonal shape, elliptical shape, diamond shape, star shape, or triangular shape, as shown in FIGS. 14-17 and FIGS. 19-23.

ECG electrode 1010 of FIG. 14 is a disposable electrode. As a result, in various embodiments, substrate 1015 comprises a sustainable and easily biogradeable material to give substrate 1015 support and to decrease the effect on the environment from the disposal of ECG electrode 1010. The sustainable material can include, but is not limited to, bamboo or seaweed.

Method for Manufacturing an ECG Electrode with Holes

Figure 25:
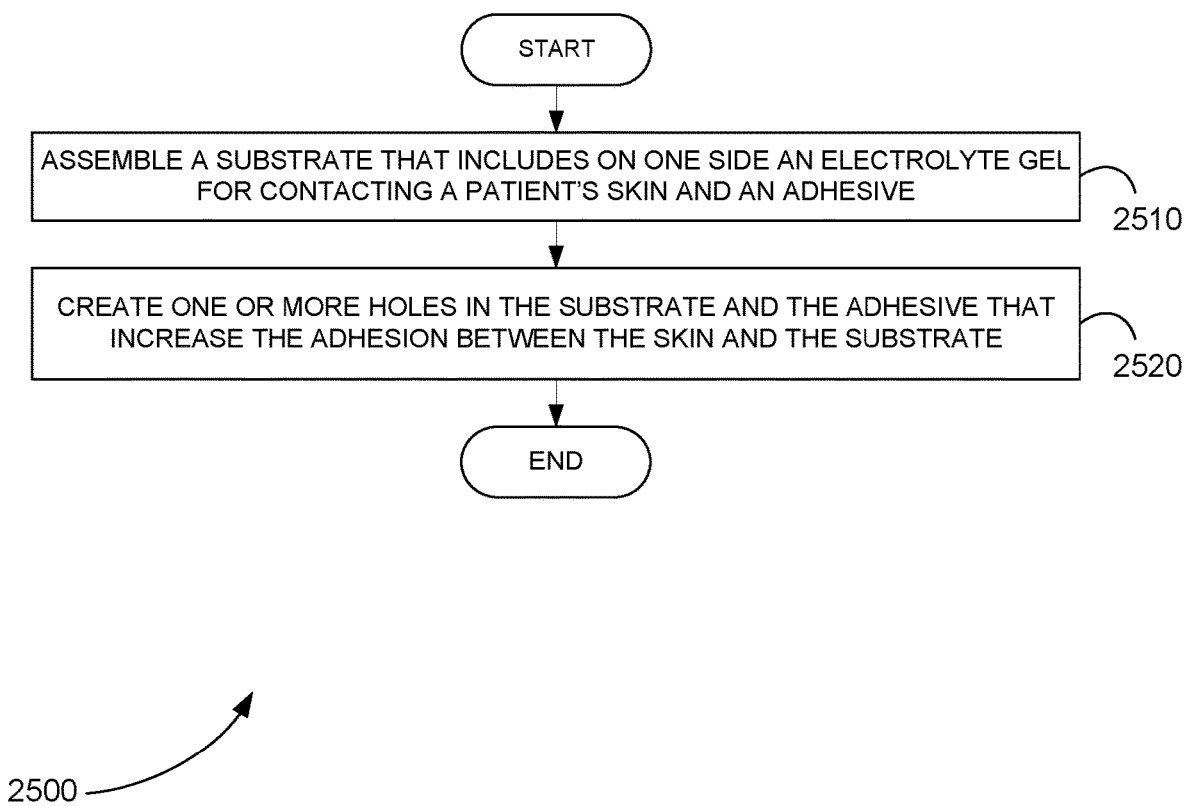
FIG. 25 is a flowchart showing a method for manufacturing an ECG electrode with holes, in accordance with various embodiments.

FIG. 25 is a flowchart showing a method 2500 for manufacturing an ECG electrode with holes, in accordance with various embodiments.

In step 2510 of method 2500, a substrate is assembled that includes on one side an electrolyte gel for contacting a patient's skin and an adhesive.

In step 2520, create one or more holes in the substrate and the adhesive that increase the adhesion between the skin and the substrate.

In various embodiments, the one or more holes are created using a laser. The one or more holes are burned through the substrate or the shape of the hole is made by scribing the shape of the hole with the laser.

In various embodiments, the one or more holes are created using a drill.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. An electrocardiography (ECG) electrode, comprising:
   an electrode substrate;
   an electrode that includes
      a layer of conductor and
      a layer of electrolyte gel for contacting with skin that in response to an electrical signal at the surface of the skin frees ions in the electrolyte gel that, in turn, cause the layer of conductor to give up electrons; and
   one or more holes that each penetrates through the electrode substrate and through the layer of electrolyte gel of the electrode to the skin to allow air to vent through the electrode substrate and through the layer of electrolyte gel of the electrode to improve tensile strength to prevent tearing and pulling from the skin.

2. The ECG electrode of claim 1, wherein the ECG electrode is a snap-type electrode.

3. The ECG electrode of claim 2, wherein the one or more holes are symmetrically positioned around a snap of the snap-type electrode.

4. The ECG electrode of claim 1, wherein the ECG electrode is a tab-type electrode.

5. The ECG electrode of claim 1, wherein the electrode substrate has a rectangular shape.

6. The ECG electrode of claim 1, wherein the electrode substrate has a circular shape.

7. The ECG electrode of claim 1, wherein the electrode substrate has a hexagonal shape.

8. The ECG electrode of claim 1, wherein the electrode substrate has a circular shape with one or more semicircular edges equally spaced along the edge of the circular shape.

9. The ECG electrode of claim 1, wherein the one or more holes include four holes symmetrically positioned on the electrode substrate.

10. The ECG electrode of claim 1, wherein one or more holes include one or more of a circular shape, rectangular shape, crescent shape, polygonal shape, elliptical shape, diamond shape, star shape, or triangular shape.

11. The ECG electrode of claim 1, wherein the electrode substrate comprises bamboo.

12. The ECG electrode of claim 1, wherein the electrode substrate comprises seaweed.

13. The ECG electrode of claim 1, wherein each hole of the one or more holes also penetrates through the layer of conductor.

14. The ECG electrode of claim 1, wherein layer of electrolyte gel is further mixed with adhesive for adhering to the skin.

15. A method for manufacturing an electrocardiography (ECG) electrode, comprising:
   assembling an electrode substrate;
   assembling on one side of the electrode substrate an electrode that includes
      a layer of conductor and
      a layer of electrolyte gel for connecting to the layer of conductor on one side and for contacting with skin on another side, wherein, in response to an electrical signal at the surface of the skin, the layer of electrolyte gel frees ions in the electrolyte gel that, in turn, cause the layer of conductor to give up electrons; and
   creating one or more holes that each penetrates through the electrode substrate and through the layer of electrolyte gel of the electrode to the skin to allow air to vent through the electrode substrate and through the layer of electrolyte gel of the electrode to improve tensile strength to prevent tearing and pulling from the skin.

16. The method of claim 15, wherein the one or more holes are created using a laser.

17. The method of claim 15, wherein the one or more holes are created using a drill.

18. The method of claim 15, wherein each hole of the one or more holes also penetrates through the layer of conductor.

19. The method of claim 15, wherein layer of electrolyte gel is further mixed with adhesive for adhering to the skin.

* * * * *